United States Patent
Dvärsäter

(10) Patent No.: US 6,569,132 B1
(45) Date of Patent: May 27, 2003

(54) MEDICAL DEVICE

(75) Inventor: Gudmund Dvärsäter, Mölndal (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/230,501

(22) PCT Filed: Dec. 15, 1998

(86) PCT No.: PCT/SE98/02317
§ 371 (c)(1),
(2), (4) Date: Jan. 26, 1999

(87) PCT Pub. No.: WO99/30652
PCT Pub. Date: Jun. 24, 1999

(30) Foreign Application Priority Data

Dec. 17, 1997 (SE) .................................. 9704712

(51) Int. Cl.⁷ .......................... A61F 5/44; A61M 31/00
(52) U.S. Cl. ..................... 604/328; 604/276; 600/29
(58) Field of Search ................ 604/328, 329, 604/331, 319, 317, 327, 326, 276; 600/29, 38

(56) References Cited

U.S. PATENT DOCUMENTS

| 1,547,127 A | * | 7/1925 | Metzger | |
| 2,291,191 A | * | 7/1942 | Scudder, Jr. | 128/294 |
| 2,691,373 A | * | 10/1954 | Breid | 128/239 |
| 3,768,476 A | * | 10/1973 | Raitto | 128/275 |
| 3,802,418 A | * | 4/1974 | Clayton | 128/2 F |
| 4,137,918 A | * | 2/1979 | Bogert | 128/283 |
| 4,263,914 A | | 4/1981 | Pawlak | 128/341 |
| 4,564,361 A | * | 1/1986 | Akiyama | 604/265 |
| 4,585,666 A | | 4/1986 | Lambert | |
| 4,596,554 A | * | 6/1986 | Dastgeer | 604/54 |
| 4,723,950 A | * | 2/1988 | Lee | 604/322 |
| 4,943,285 A | * | 7/1990 | Hawks | 604/275 |
| 6,110,483 A | * | 8/2000 | Whitborne et al. | 424/423 |

FOREIGN PATENT DOCUMENTS

| EP | 0 217 771 A1 | * | 4/1987 | ............. C08J/7/04 |
| SU | 1296150 | | 3/1987 | |
| SU | 1727826 | | 4/1992 | |
| WO | WO-94/20059 | * | 9/1994 | ......... A61H/21/00 |

* cited by examiner

Primary Examiner—Weilun Lo
Assistant Examiner—Michael Bogart
(74) Attorney, Agent, or Firm—White & Case LLP

(57) ABSTRACT

Rectal insertion device (1) for treating disorders of the digestive tract of a human or animal body such as colic comprising an elongate shaft (3) which is insertable into the anal canal of the human or animal body and a receptacle (12) for collecting feces discharged when the elongate shaft is inserted into the anal canal.

15 Claims, 1 Drawing Sheet

MEDICAL DEVICE

FIELD OF THE INVENTION

Figure 1:
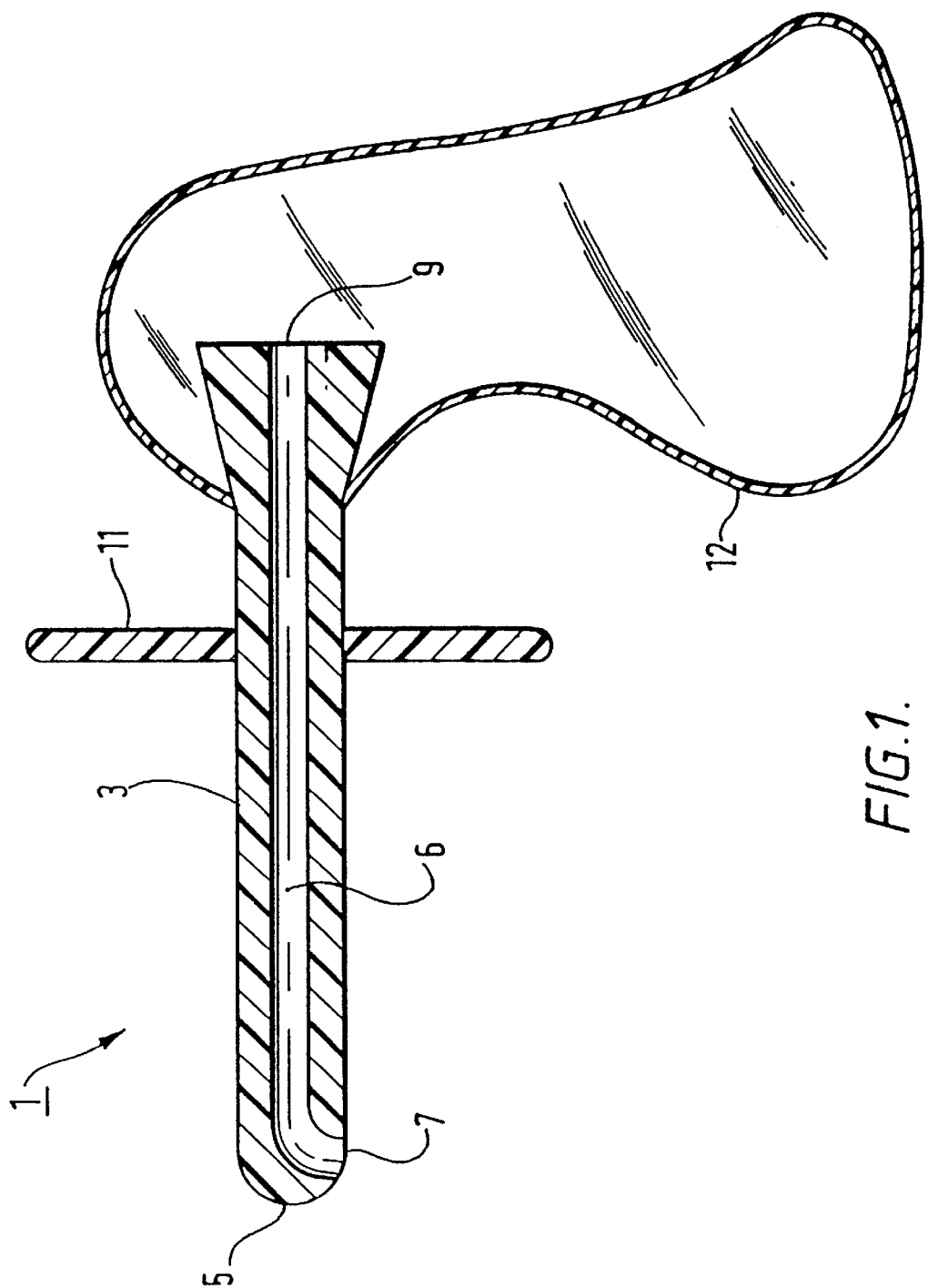

The present invention relates to a rectal insertion device for treating disorders of the digestive tract in human or animal bodies such as colic, including infantile colic, hemorrhoids, constipation, gas, piles and the like.

BACKGROUND OF THE INVENTION

A rectal insertion device for treating colic, constipation and gastrointestinal gases is disclosed in International patent application publication WO94/20059. The rectal insertion device takes the form of a solid rod of a diameter small enough to fit into the anal canal but wide enough to sufficiently stimulate the sphincter muscles without completely filling the anal canal. The device is used to treat colic, constipation and gastrointestinal gases by moving the rod back and forth in the anal canal to stimulate the sphincter muscles until gastrointestinal gases are released over the outer surface of the rod. A transversely extending plate is provided on the rod between the proximal and distal ends to delimit insertion of the rod into the anal canal and also to serve as a handle. To assist insertion of the rod it is suggested that the rod be lubricated immediately prior to use with a lubricant such as glycerine or petroleum jelly.

U.S. Pat. Nos. 4,263,914, 1,042,624 and 1,547,127 also make known rectal insertion devices in the form of rods for treating rectal diseases such as hemorrhoids and piles. In these devices, the rods are provided with a central lumen which extends between an opening in the tip at the distal end of the rod and an opening in the proximal end of the rod. It is also suggested for some of these devices that insertion into the anal canal would be facilitated by lubricating the outer surface of the rod immediately beforehand, for example with Vaseline®.

A problem with the hitherto proposed devices is that no provision is made for capturing the feces discharged through the anal canal as a result of their application. The aim of the present invention is to address this problem.

DISCLOSURE OF THE INVENTION

According to the present invention there is provided a rectal insertion device for treating disorders of the digestive tract in a human or animal body comprising an elongate shaft which is insertable into the anal canal of the human or animal body and a receptacle for collecting feces discharged from the anal canal when the elongate shaft is inserted into the anal canal.

In an embodiment of the invention such as the one hereinafter to be described, the receptacle is coupled to the proximal end of the elongate shaft.

In an embodiment of the invention such as the one hereinafter to be described, the shaft is provided with a lumen which extends between a proximal opening in the proximal end of the elongate shaft and a distal opening in the distal end of the elongate shaft and the receptacle communicates with the proximal opening of the lumen. The receptacle may be made of a material which is gas permeable thereby to allow gastrointestinal gases discharged through the lumen of the device to pass through the receptacle.

In an embodiment of the invention such as the one hereinafter to be described, the rectal insertion device is provided with means for controlling the degree of insertion of the elongate shaft into the anal canal, for example a transversely extending plate-like element mounted on the shaft.

In an embodiment of the invention such as the one hereinafter to be described, the elongate shaft is preformed with a friction-reducing coating on the outer surface thereof. This negates the requirement with the previous devices to lubricate the outer surface with a jelly or the like immediately prior to use. The friction-reducing coating may be a hydrophilic coating which has a reduced friction when wetted, for example a coating formed from polyvinyl pyrrolidone.

The elongate shaft of the rectal insertion device may be presented by a urethral drainage catheter and the receptacle by a urine collection bag.

In an embodiment of the invention, the elongate shaft of the rectal insertion device is adapted for insertion into the anal canal of a human infant body whereby disorders of the digestive tract of the human infant body such as infantile colic are treatable.

According to the present invention, there is further provided a kit for the treatment of disorders of the digestive tract in a human or animal body comprising a structure which presents an elongate shaft which is insertable into the anal canal of the human or animal body and a receptacle which is adapted to be coupled to the structure for collecting discharged feces when the elongate shaft is inserted into the anal canal.

DESCRIPTION OF EXEMPLARY EMBODIMENT OF THE INVENTION

By way of example, an embodiment of the invention will now be described with reference to the accompanying FIGURE which shows in cross-section a rectal insertion device 1 for treating digestive disorders such as colic in human patients comprising a thermoplastic elongate shaft 3 having a closed tip 5 at the distal end thereof and a lumen 6 which extends between a distal opening 7 in the tip 5 and a proximal opening 9 in the proximal end of the shaft 3. The diameter of the shaft will typically be in the range of about 3–6 mm when for use with infants and in the range of about 6–15 mm when for use with adults.

In use, the tip 5 of the shaft 3 is positioned just past the external sphincter muscles at the entry point to the anal canal thereby enabling the sphincter muscles to be stimulated if need be and gastrointestinal gases and feces to be discharged through the lumen 6. The insertable length of the shaft 3 for adults would ordinarily be anywhere up to 20 mm and in the range of about 5–10 mm for infants. With this in mind, the device 1 further comprises a plate 11 mounted on the shaft 3 to limit the degree of insertion of the shaft 3 into the anal canal to prevent damage to the rectum and large intestine.

To facilitate insertion of the shaft, at least a substantial portion of the outer surface of the insertable length of the shaft 3 is preformed with a hydrophilic outer surface coating, for example a polyvinyl pyrrolidone-based hydrophilic outer surface coating applied in accordance with one of the methods disclosed in European patent Nos. 0,093,093 and 0,217,771.

For greater efficiency of release of gastrointestinal gases and feces the distal portion of the insertable length of the shaft 3 may be provided with further openings which communicate with the lumen 6.

While the provision of the plate 11 is preferable it is of course entirely optional. Other means of controlling the extent of insertion of the shaft 3 could be provided, for instance markings on the shaft 3, or dispensed with completely. If the plate 11 is dispensed with then the shaft 3 could simply be a "converted" surface coated urethral drainage catheter, for instance the hydrophilic surface coated urinary catheter marketed by Astra Tech AB, Mölndal, Sweden under the trade mark LoFric®. Of course, the shaft 3 of the device 1 shown could be formed by such a urethral drainage catheter with the plate 11 being added thereto.

Attached to the proximal end of the elongate shaft 3 is a bag 12 for collecting feces discharged through the lumen 6. The proximal end of the shaft 3 is flared so as to form a mechanical seal with the opening of the bag 12 as shown. The shaft 3 (with or without the plate 11) could be packaged inside the bag 12 with an opening being made in the bag just prior to use for the shaft 3 to be pushed through until the mechanical seal is formed. Where the plate 11 is included, the shaft 3 would be pushed through the opening in the bag 12 until the plate 11 forms a seal with the opening, that is to say, the plate 11 would remain in the bag 12. This type of arrangement is already known from International patent application publication No. WO97/26937 and UK patent application publication No. 2284764 for combining a urethral drainage catheter with a urine collection bag for collecting urine from the bladder and the contents of these two publications relating to this feature are incorporated herein by reference.

What is claimed is:

1. A rectal insertion device for treating disorders of the digestive track of a patient, the device comprising:
   (a) an elongate shaft having a distal end which is insertable into the anal canal of the patient and a proximal end, wherein the distal end of the shaft is structurally shaped for inward and outward motion while the device is within the anal canal and the distal end of the shaft is free of means capable of substantially limiting the inward and outward motion of the device while the device is within the anal canal, and
   (b) a receptacle for collecting feces discharged when the elongate shaft is inserted into the anal canal.

2. The rectal insertion device according to claim 1, wherein the receptacle is coupled to the proximal end of the elongate shaft.

3. The rectal insertion device according to claim 1, wherein the elongate shaft is provided with a lumen which extends between a distal opening in the distal end of the elongate shaft and a proximal opening in the proximal end of the elongate shaft and wherein the receptacle communicates with the proximal opening of the lumen.

4. The rectal insertion device according to claim 1, wherein the elongate shaft is preformed with a friction-reducing coating on an outer surface thereof.

5. The rectal insertion device according to claim 4, wherein the friction-reducing coating is a hydrophilic coating which has a reduced friction when wetted.

6. The rectal insertion device according to claim 1, wherein insertion control means are provided for controlling the degree of insertion of the elongate shaft into the anal canal.

7. The rectal insertion device according to claim 6, wherein the insertion control means comprises a transversely extending plate-like element mounted on the shaft.

8. The rectal insertion device according to claim 1, wherein the diameter of the elongate shaft is in the range of 3–15 mm.

9. The rectal insertion device according to claim 8, wherein the diameter of the elongate shaft is in the range of 3–6 mm.

10. The rectal insertion device according to claim 1, wherein the elongate shaft comprises an insertable length of up to 20 mm.

11. The rectal insertion device according to claim 10, wherein the insertable length is in the range of 5–10 mm.

12. The rectal insertion device according to claim 1, wherein the elongate shaft is movable back and forth in the anal canal to stimulate the sphincter muscles.

13. The rectal insertion device according to claim 1, wherein the insertable end of the elongate shaft is rounded.

14. The rectal insertion device according to claim 1, wherein the elongate shaft is adapted for insertion into the anal canal of a human infant.

15. A kit for the treatment of disorders of the digestive tract in a patient, the kit comprising:
   (a) a structure which presents an elongate shaft having a distal end which is insertable into the anal canal of the patient and a proximal end, wherein the distal end of the shaft is structurally shaped for an inward and outward motion while the device is within the anal canal, and the distal end of the shaft is free of means capable of substantially limiting the inward and outward motion of the device while the device is within the anal canal, and
   (b) a receptacle which is adapted to be coupled to the structure for collecting discharged feces when the elongate shaft is inserted into the anal canal.

* * * * *